US012766299B2

(12) United States Patent
Sedky et al.

(10) Patent No.: US 12,766,299 B2
(45) Date of Patent: Oct. 20, 2026

(54) MICRONEEDLE INTEGRATED 3D PRINTED MICROPUMP COMBINED WITH POLYMERIC NANOPARTICLES FOR RAPID RELEASE TRANSDERMAL DRUG DELIVERY

(71) Applicant: The American University in Cairo, New York, NY (US)

(72) Inventors: Mostafa Sedky, New Cairo (EG); Ahmed Abdelnabi, New Cairo (EG); Mona Abdel-Mottaleb, New Cairo (EG); Mohamed Yousef Serry, Cairo (EG)

( * ) Notice: Subject to any disclaimer, the term of this patent is extended or adjusted under 35 U.S.C. 154(b) by 0 days.

(21) Appl. No.: 18/931,328

(22) Filed: Oct. 30, 2024

(65) Prior Publication Data

US 2025/0144387 A1 May 8, 2025

Related U.S. Application Data

(60) Provisional application No. 63/596,345, filed on Nov. 6, 2023.

(51) Int. Cl.
*A61M 37/00* (2006.01)
*F03G 7/06* (2006.01)

(52) U.S. Cl.
CPC . *A61M 37/0015* (2013.01); *A61M 2037/0023* (2013.01); *A61M 2037/003* (2013.01);
(Continued)

(58) Field of Classification Search
CPC .. A61M 2037/0023; A61M 2037/0061; A61M 2205/0266; A61M 2205/0272;
(Continued)

(56) References Cited

U.S. PATENT DOCUMENTS 6,939,323 B2 * 9/2005 Angel ................. F03G 7/06143 60/528
10,907,625 B2 2/2021 Oakes
(Continued)

FOREIGN PATENT DOCUMENTS

CN 107781124 A * 3/2018 ............. F03G 7/065

OTHER PUBLICATIONS

Guo et al. SMA Actuator-based Novel Type of Peristaltic Micropump. http://dx.doi.org/10.1109/ICINFA.2008.4608263.
(Continued)

*Primary Examiner* — Emily L Schmidt
*Assistant Examiner* — Martin A Radomski

(57) ABSTRACT

A transdermal drug delivery (TDD) system is provided accelerating the TDD process through the combination of (1) a micropump, (2) microneedles, and (3) nanoencapsulation. A 3D printed shape memory alloy (SMA) triggered micropump combined with polymeric nanoparticles loaded with a drug can be pumped through integrated microneedles. An SMA spring wire is used to actuate a loaded pumping spring to drive an elastic membrane into a chamber. The system's performance characterized an average membrane speed of 0.28 m/s. The efficacy of the system showed an almost 100% improvement for the total percentage of deposited polymeric nanoparticles over that of the untreated solution. The rapid response and demonstrated efficacy can be aimed for transdermal insulin injection.

2 Claims, 7 Drawing Sheets

(52) U.S. Cl.
CPC ............... *A61M 2037/0061* (2013.01); *A61M 2205/0266* (2013.01); *A61M 2205/106* (2013.01); *F03G 7/06145* (2021.08)

(58) Field of Classification Search
CPC . A61M 60/451; A61M 60/484; F04B 43/043; F03G 7/065; F03G 7/06145
USPC .......................................................... 604/506
See application file for complete search history.

(56) References Cited

U.S. PATENT DOCUMENTS

| | | | | |
|---|---|---|---|---|
| 11,311,670 | B2 * | 4/2022 | Barmaimon | A61M 5/31511 |
| 2003/0229310 | A1 * | 12/2003 | Flaherty | A61M 5/1452<br>604/151 |
| 2005/0238506 | A1 * | 10/2005 | Mescher | F04B 35/045<br>417/413.1 |
| 2006/0260534 | A1 * | 11/2006 | Petrakis | G01K 5/483<br>374/E1.002 |
| 2011/0173969 | A1 * | 7/2011 | Vaidyanathan | F03G 7/06145<br>60/527 |
| 2017/0290975 | A1 * | 10/2017 | Barmaimon | F03G 7/0646 |

OTHER PUBLICATIONS

Kortb et al. Shape Memory Alloy Capsule Micropump for Drug Delivery Applications. doi: 10.3390/mi12050520.

* cited by examiner

MICRONEEDLE INTEGRATED 3D PRINTED MICROPUMP COMBINED WITH POLYMERIC NANOPARTICLES FOR RAPID RELEASE TRANSDERMAL DRUG DELIVERY

CROSS-REFERENCE TO RELATED APPLICATIONS

This application claims priority from U.S. Provisional Patent Application 63/596,345 filed Nov. 6, 2023, which is incorporated herein by reference.

FIELD OF THE INVENTION

This invention relates to drug delivery devices, methods and systems.

BACKGROUND OF THE INVENTION

Transdermal drug delivery (TDD) is a prominent method for administering drugs through the skin that has been continuously explored for almost 50 years. This method provides a painless, less intrusive (sometimes even non-invasive) approach to administering drugs for motion sickness, smoking cessation, dementia, type 1 diabetes, and several other ailments. Currently developed TDD systems utilize MNs and/or nanoencapsulated drugs, which need time (typically 1~6 hours) for a controlled, sustained release to fully ensue. This makes these systems unsuitable for rapid release requirements, which are a necessity for placating the effects of many ailments. A need, therefore, exits for a system that benefits from the painless delivery of TDD while providing rapid release of the drug into the user. In this context, with this invention, such a system is explored through the combination of (1) microneedles (MNs), (2) nanoencapsulated drug, and (3) micropumps.

SUMMARY OF THE INVENTION

A transdermal drug delivery (TDD) device, method and/or system has been devised, integrating a Shape Memory Alloy (SMA) activated micropump, microneedles (MNs), and nanoencapsulation for accelerated drug release, marking a significant advancement in the field. Embodiments of the invention leverage the compactness of a 3D-printed, SMA-triggered micropump, the inventors have achieved enhanced precision in drug delivery. The inventors' introduction of polymeric nanoparticles offers a revolutionary leap in drug deposition, outperforming conventional methods.

Through ex vivo skin studies, the inventors have showcased a marked elevation in the deposition efficiency of these polymeric nanoparticles versus traditional drug mediums.

The low power consumption, swift responsiveness, and compatibility with wearable integration signals a transformative potential for transdermal insulin administration.

Key aspects of the invention are:

1. Integration of nanoencapsulation for enhanced drug deposition: The integration of nanoencapsulated drugs with this rapid-delivery system allows for efficient skin absorption. Polymeric nanoparticles, which are generally used to prolong drug retention within tissues, here serve a dual role: 1. they enable deep penetration into skin layers, and 2. they provide an initial burst of drug deposition when combined with the micropump's mechanical action. This synergistic integration of nanoparticles into the micropump for both immediate and sustained release in a single system is innovative and not evident from prior art approaches that consider these functions separately.
2. Unique role of the SMA spring for triggering rather than pumping: In this system, the SMA spring is only used as a trigger mechanism rather than as a direct actuator for pumping. This reduces the complexity and energy consumption of the mechanism compared to that of a traditional SMA-based micropump where the spring could also unfavorably heat the drug (as it is wrapped around it during pumping). The SMA spring's contraction triggers a controlled release mechanism, which then allows a pre-loaded spring to drive the fluid through the hollow microneedles. This separation of roles is not evident in existing designs, where SMA is often employed as the primary actuator for fluid movement.
3. Compact design: The invention achieves this functionality within a compact and energy-efficient design that is suitable for wearable applications. The use of a small SMA-triggered mechanism allows the entire system to be miniaturized without compromising its power or speed of delivery. This level of miniaturization, combined with a high-speed release capability, is particularly advantageous for portable, patient-friendly devices.
4. Precision control of drug delivery speed: The actuation speed of the membrane is controlled by the interaction between the pre-loaded spring, the SMA-triggered release, and the damping foam. This provides a design space for precise control over the pressure applied for drug deposition.

The present invention can further be characterized as a transdermal drug delivery method where a transdermal drug delivery system is used. This system has (i) a triggering subsystem with a Shape Memory Alloy (SMA) spring attached and above an iron trigger, (ii) a drug delivery subsystem situated below the triggering subsystem, where the drug delivery subsystem has a preloaded pumping spring situated above a magnet, and as such the preloaded pumping spring is positioned in between the iron trigger and the magnet, and (iii) a microneedle subsystem with a pump chamber containing a drug (e.g. a nanoencapsulated drug), an elastic membrane lining an inside of the pump chamber, and an array of hollow microneedles at a bottom of the pump chamber. A current to the SMA spring is controlled that results in the SMA spring to heat and shrink to an original length of the SMA spring. This heating and shrinking separates the SMA spring and attached iron trigger from the magnet resulting in extension of the preloaded pumping spring. The extension of the preloaded pumping spring results in pushing the drug in the pump chamber through the elastic membrane and then through the array of hollow microneedles. In case the array of hollow microneedles is in contact with a skin portion, the drug is pushed into the skin portion via the array of hollow microneedles.

BRIEF DESCRIPTION OF THE DRAWINGS

Numbering and Labels in Figures:

100 Transdermal drug delivery.
110 SMA trigger mechanism or subsystem.
120 Drug delivery mechanism or subsystem.
130 Microneedle subsystem.
140 Pump cover.

Figure 1A:
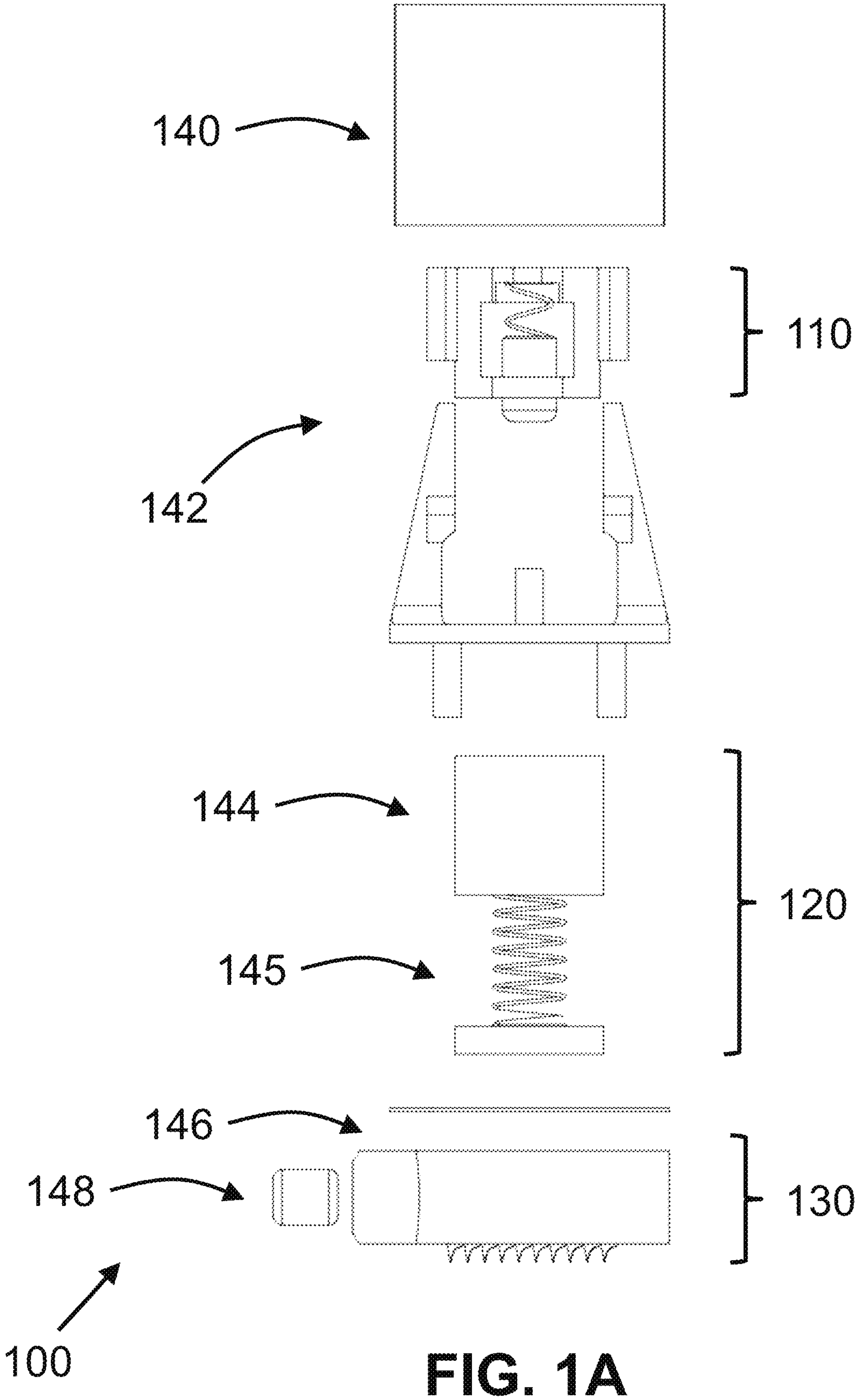

142 Both parts indicated are top of pump casing in exploded view.

144 Damping foam

145 Pumping spring

146 Pumping chamber

148 Self-healing inlet

150 Shape Memory Alloy (SMA) spring

152 Iron Trigger

154 Pumping membrane

156 Magnet

158 Microneedles

FIG. 1A shows an exploded view of the micropump assembly according to an exemplary embodiment of the invention.

Figure 1B:
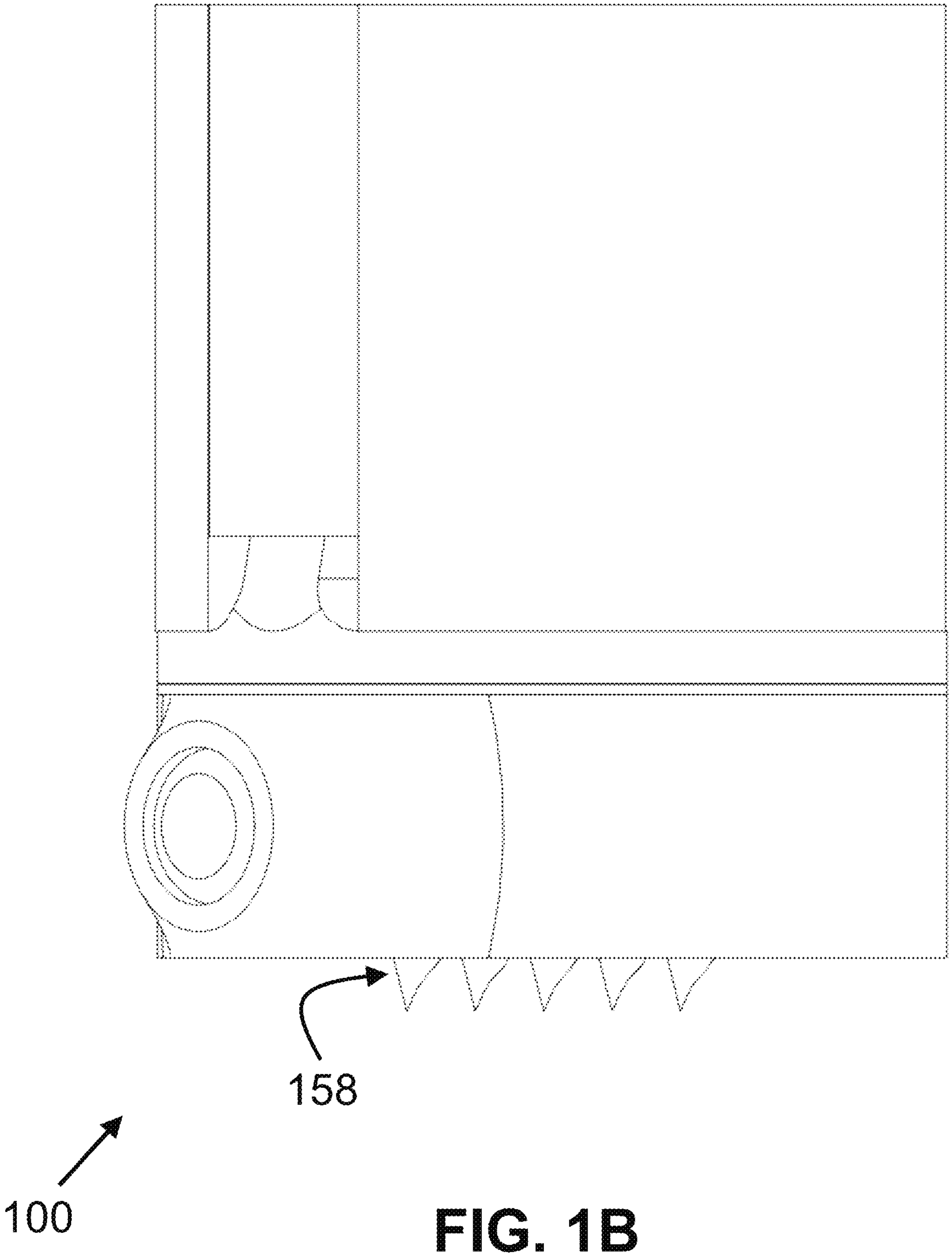

FIG. 1B shows an isometric view of the pumping system according to an exemplary embodiment of the invention.

Figure 1C:
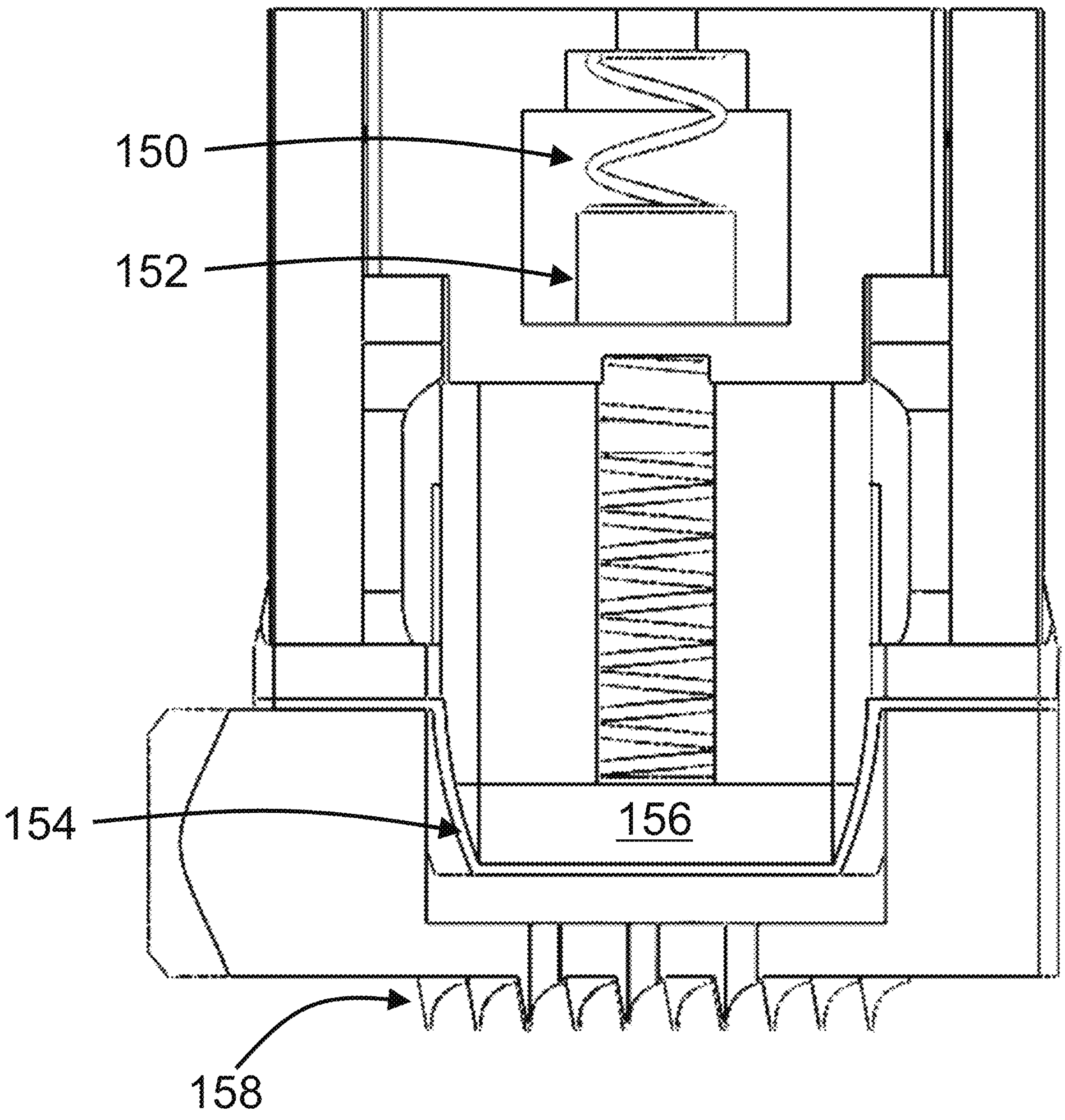

FIG. 1C shows a detailed view of the SMA trigger and drug delivery system according to an exemplary embodiment of the invention.

Figure 2A:
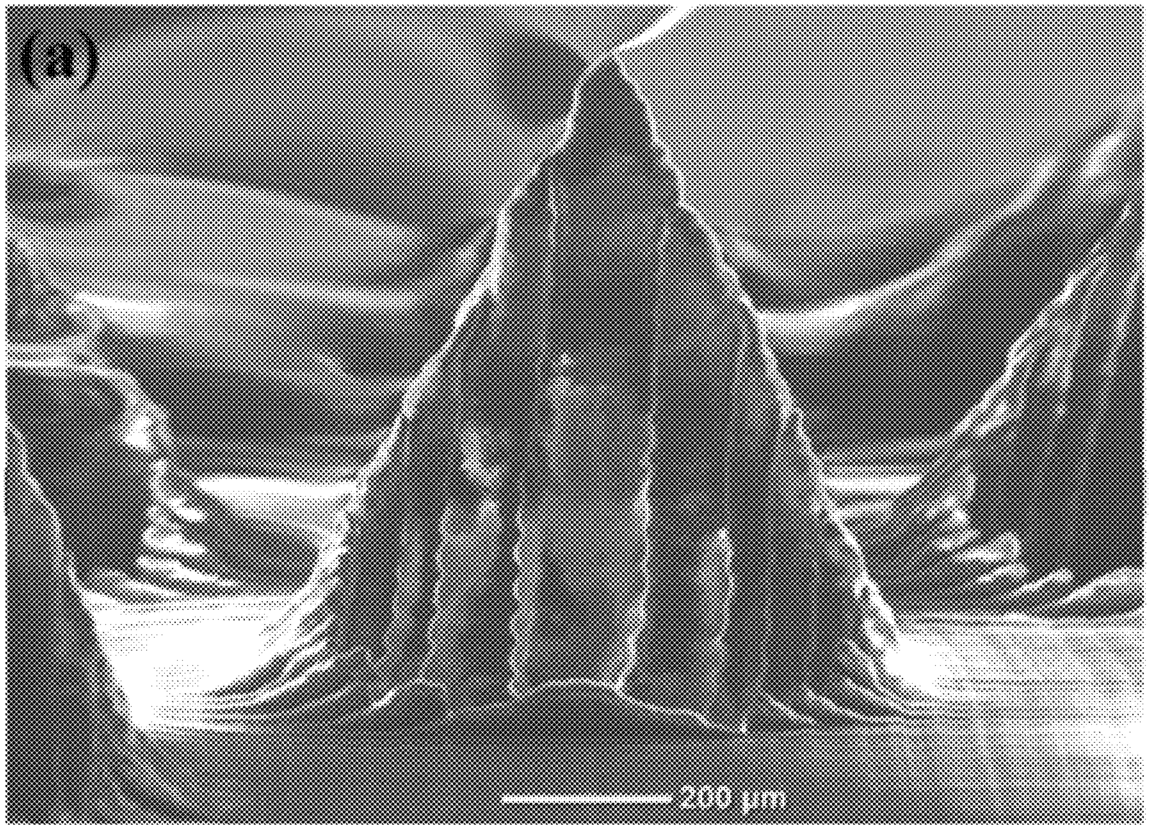
Figure 2B:
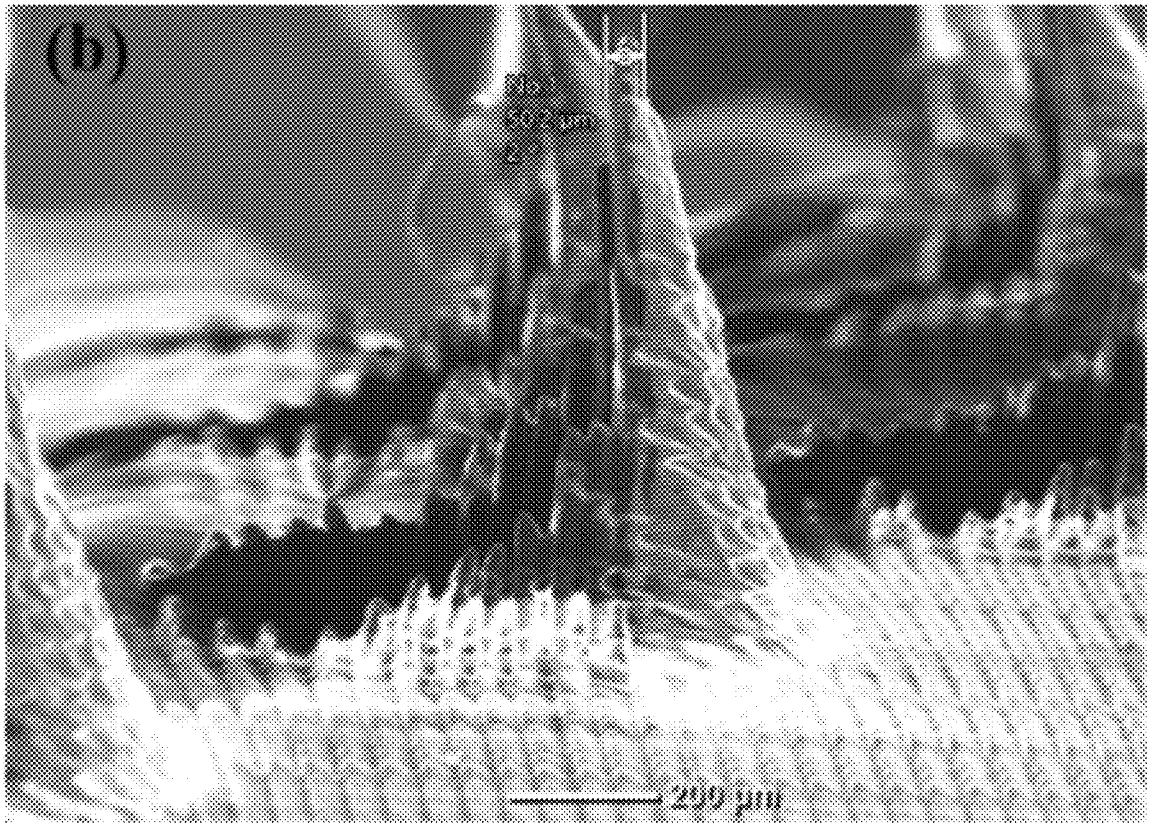

FIG. 2A-B show the hollow microneedle design and fabrication according to an exemplary embodiment of the invention with in FIG. 2A a front view SEM image of a fabricated microneedle, and in FIG. 2B a side view SEM image of a microneedle showing the tip diameter.

Figure 3:
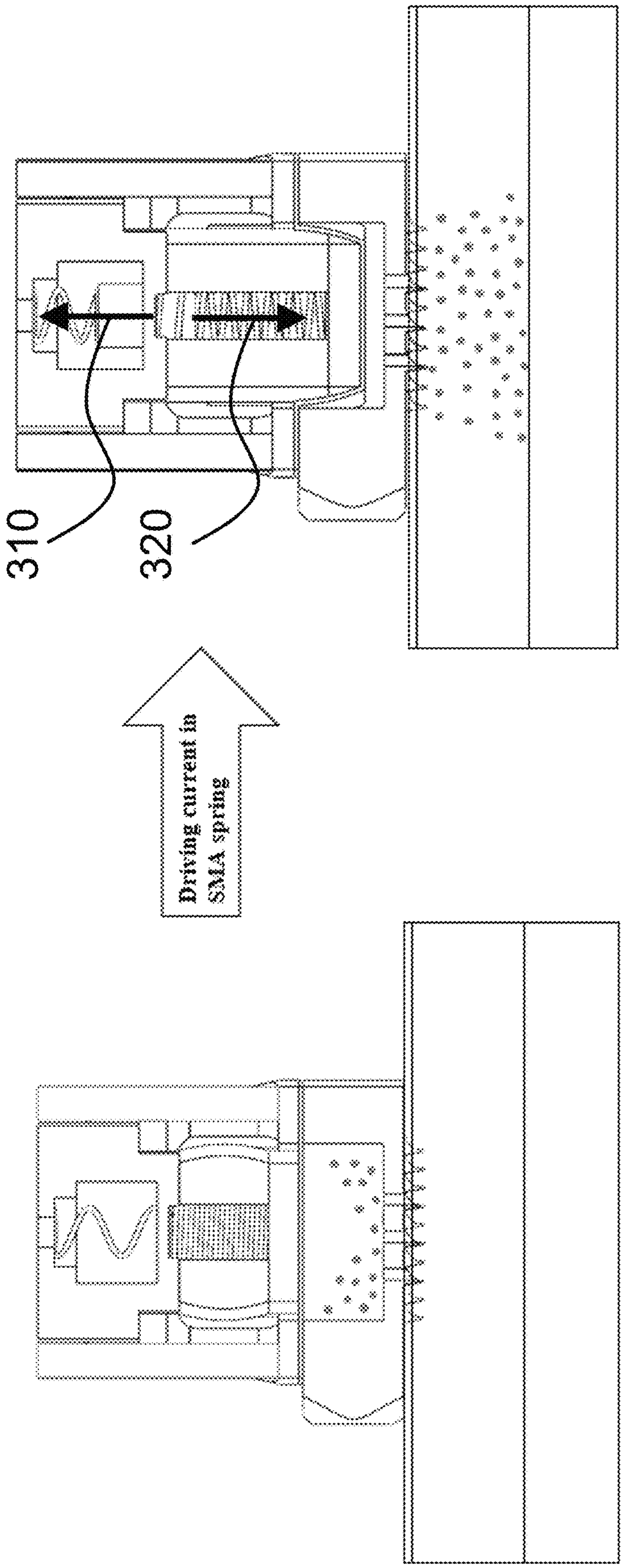

FIG. 3 shows according to an exemplary embodiment of the invention the micropump triggering mechanism. Dots represent the drug. Arrow 310 indicates an upward motion of the iron core (iron trigger) due to the SMA spring shrinkage and arrow 320 indicates a downward motion of the preloaded pumping spring after trigger.

Figure 4A:
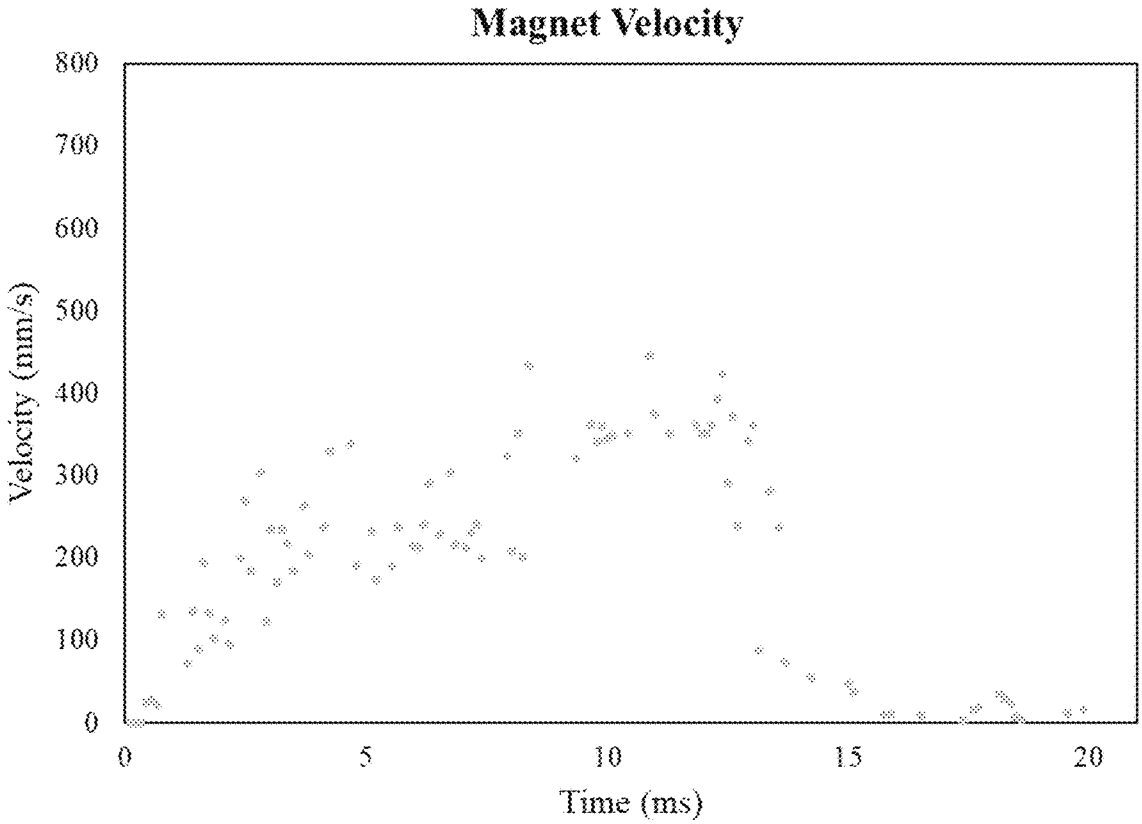
Figure 4B:
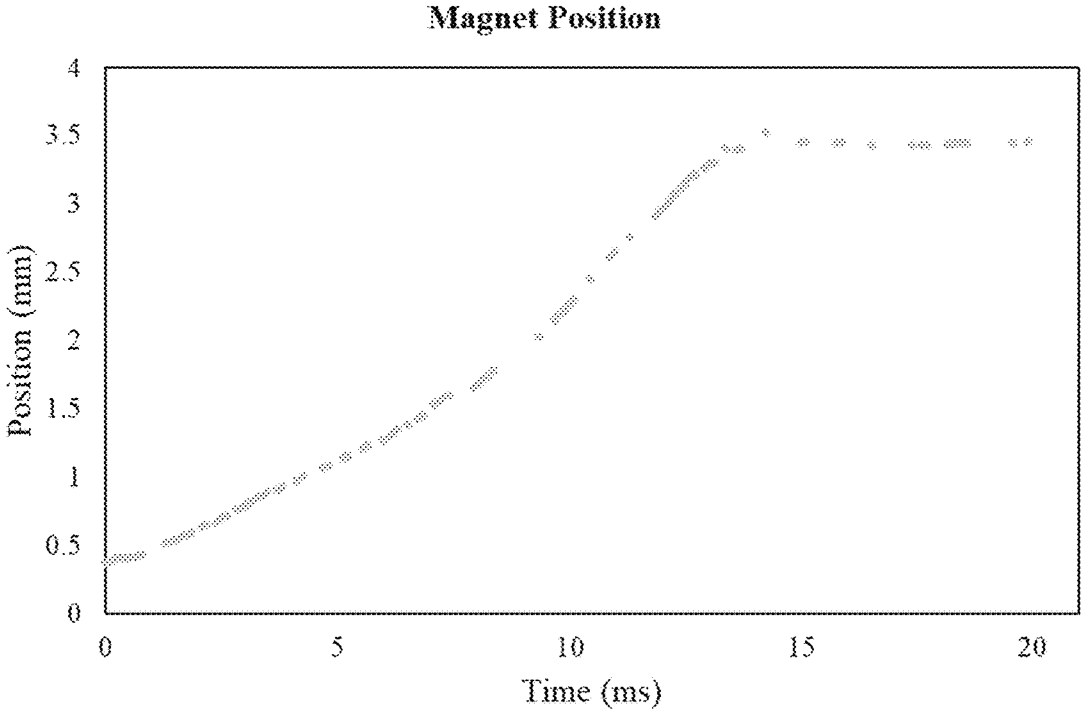

FIG. 4A-B show the according to an exemplary embodiment of the invention micropump actuation high-speed imaging results. (FIG. 4A) Magnet position showing a 299-maximum stroke of 3.6 mm. (FIG. 4B) Magnet velocity showing a maximum velocity of 0.45 m/s and 300 an average velocity of 0.28 m/s.

DETAILED DESCRIPTION

Transdermal drug delivery (TDD) systems can take many forms, but they all serve the same general function. A TDD system transports a drug from outside the body to the blood vessels inside the skin. The skin is a complex multilayered organ which two main components: the epidermis and the dermis. The epidermis, typically 75 to 150 μm in thickness for humans, serves as a layer of protection to the dermis, which is a much thicker (1 to 4 mm) layer that contains capillary blood vessels, sweat ducts, hair follicles, and pain receptors.

One of the most popular and actively researched forms of TDD systems is the microneedle drug delivery system. This is primarily due to the relative ease of manufacturing and customization of such needles with technologies that have seen a drastic improvement in precision over the past decade like additive manufacturing. Microneedle systems pierce through the epidermis layer to deliver the drug into the dermis layer containing the blood vessels without reaching the pain receptors, providing a painless drug delivery process. 3D printing has become an increasingly popular fabrication method for MN systems. Stereolithography (SLA) has been extensively utilized to fabricate a multitude of MN designs because of the versatility, rapid prototyping capability, and relatively remarkable precision made possible by the recent integration of 4K LCD screens in SLA printers.

MN systems can generally be characterized by their design configuration. Solid MNs, for example, are designed to either have a dry drug coat that is released in the skin after piercing the epidermis layer or to have the drug subsequently released in the skin after the MNs have breached the epidermis. Dissolving MNs fully dissolve into the skin, releasing the drug in the process. Hollow MNs, however, allow the drug to reach the dermis through the interior of the MNs. The present invention work focuses on hollow MNs because of the ease of integrating this type of MN design with a controlled or rapid release device (e.g. micropumps) for automated drug delivery.

The integration of micropumps with hollow MNs is an idea that has proven successful in recent studies. This integration provides an element of control over the system which can potentially be combined with machine learning tools to automatically estimate the patient's need for the right dosage. The challenge, however, partly lies in realizing a small enough and easy to manufacture micropump design that can be seamlessly integrated with the MN array. Piezoelectrically actuated, shape memory alloy (SMA) actuated, electromagnetically actuated, and several more actuating mechanisms have been developed over the past two decades to create small footprint micropump designs. 3D printing techniques such as SLA and fused deposition modeling (FDM) have also been utilized to fabricate complicated micropump designs with little difficulty.

MNs have also been combined with the use of nanoparticles to enhance the drug's absorption rate into the skin. Polymeric nanoparticles were found to significantly enhance the deposition into the skin leading to localized sustained release into the skin layers of the loaded drugs. This could be owed to the solid nature of these carriers compared to other types of lipidic nanosystems, which tend usually to disintegrate and diffuse through the skin layers. The use of biodegradable polymers such as PLGA (poly lactic-co-glycolic acid) enhances the biocompatibility of the particles with minimal risks of skin irritation or immune reactions.

In this invention, addressing shortcomings in the art, a novel idea is presented by combining three key components: MNs, SMA triggered micropump, and drug nanoencapsulation. This serves to provide a short-term release system that benefits from TDD's painless delivery method while maintaining a small footprint in a single integrated unit. The resulting system is mostly fabricated using FDM and SLA 3D printed components to benefit from the technologies' versatility and rapid prototyping capability. Finite element analysis methods has been employed to optimize the system's MN arrangement and actuation speed for maximum drug penetration into the skin. A modal analysis study has been then performed to simulate the system's robustness under typical operating conditions (e.g. vibrations from driving a car). The micropump's actual actuation speed was characterized via high-speed camera imaging at 9200 frames per second. The MNs and formulated nanoparticles was characterized by dynamic light scattering and scanning electron microscopy (SEM) for size, zeta potential and morphology validation. The system was finally used to perform an ex vivo skin deposition test using rat skin to evaluate the efficacy of the developed framework.

Design and Principle of Operation

Overall System Design

FIG. 1A delineates a rendered exploded view of the system 100. The system has three main subsystems: SMA trigger mechanism or subsystem 110, drug delivery mechanism or subsystem 120, and microneedle subsystem 130. The main function of the SMA trigger mechanism subsystem 110 is to receive a current signal from a controller (not shown)—due to a sensor reading, for example—to trigger the drug delivery mechanism 120. This is achieved when a current flows through the SMA spring 150 (FIG. 1C), which causes it to heat and shrink to its original solid length. This triggers the movement of the drug delivery subsystem 120 when a separation between the iron trigger 152 (attached to the SMA spring 150) and the magnet 156 occurs. The drug delivery subsystem 120 then pushes the drug through a pump chamber 146 integrated with MNs 158.

In an exemplary embodiment, the inside of the pump's pumping chamber 146 is 9.7 mm in diameter and 4 mm in height to provide a theoretical total pumping volume of ~295.6 $mm^3$. The pump's outer dimensions measure 18×16×15 $mm^3$. The SMA spring 150 (Kellogg's Research Labs, USA) is a nitinol squared and ground ends compression spring with a wire diameter of 0.25 mm, mean diameter of 3 mm, 2 turns, free length of 5 mm, and solid length of 2 mm. The pumping spring 145 is also a squared and ground ends compression spring with a free length of 10 mm, mean diameter of 3 mm, solid length of 2 mm, and a spring constant of 72.5 N/m (section infra the details behind the selection of this pumping spring 145). The iron trigger 152 is a cylinder with a diameter and height of 3 mm and 4 mm, respectively. The magnet 156 utilized is an N52 grade cylindrical neodymium magnet 8 mm in diameter and 2 mm in height.

The pump's top casing 142 is fitted into the pumping chamber 146 with pins that pass through the membrane 154. The pumping spring 145 is fitted from one end through a guide in the top pump casing 142 that holds it firmly in place and the other end is fixed to the magnet 156 via an adhesive (Akfix 705). The pumping spring 145 is also fitted through the inner diameter of a cylindrical hollow damping memory foam 144 (Royal Foam, Egypt) with an outer diameter of 8 mm and height of 10 mm. The SMA spring 150 is similarly fitted in the top pump casing 142 and fixed to the iron trigger 152 with the same adhesive.

Microneedles

Hollow MNs 158 were designed with an approach similar to that of Yeung (C. Yeung et al., "A 3D-printed microfluidic-enabled hollow microneedle architecture for transdermal drug delivery," *Biomicrofluidics*, vol. 13, no. 6, November 2019, doi: 10.1063/1.5127778). FIG. 2A shows an SEM image of the fabricated microneedles. An array of 5×6 needles was integrated into the pump's pumping chamber 146 and printed as one piece using a Creality Halot Sky SLA printer. Creality's proprietary HALOT BOX software was used for slicing the CAD model to prepare it for printing. In one embodiment, the microneedles are 600 μm in length (excluding the base) with a 50 μm tip.

Pumping Mechanism

The pump's triggering mechanism is shown in FIG. 3. A 200-mA current is driven through the SMA spring 150 which heats it and causes it to contract (indicated by arrow 310) to a solid length of 2 mm, pulling the triggering iron cylinder 152 with it in the process. A separation between the magnet 156 and the iron trigger 152, therefore, takes place. This allows the pumping spring 145 and damping foam 144 to extend (indicated by arrow 320), which drives the elastic membrane 154 into the pumping chamber 146, emptying its contents in the process.

Actuation Speed

The pumping speed is primarily determined by the stiffness k and the damping coefficient c of the pumping spring and the foam damper, respectively. Assuming that the magnetic attraction between the iron trigger and the magnet is negligible after separation compared to the force of the spring (because of the quick actuation of the SMA spring producing a large enough separation), the resulting system after triggering would be a typical spring-mass-damper system with no external force. In 1D, this can be written as $$m\ddot{x} + c\dot{x} + kx = 0 \tag{1}$$

Where m is the effective mass of the spring and the magnet, c is the damping coefficient, and k is the stiffness of the system. This means that the peak time (time where the system reaches its maximum amplitude) can be found from solving Eq. 1 as $$T_p = \frac{\pi}{\omega_n\sqrt{1-\xi^2}} \tag{2}$$

$$\text{Where } \omega_n = \sqrt{\frac{k}{m}}$$

is the natural frequency and $$\xi = \frac{c}{2\sqrt{mk}}$$

is the damping ratio of the system. Following Hou (P. Hou, F. Zheng, C. D. Corpstein, L. Xing, and T. Li, "Multiphysics Modeling and 502 Simulation of Subcutaneous Injection and Absorption of Biotherapeutics: Sensitivity 503 Analysis," *Pharm Res*, vol. 38, no. 6, pp. 1011-1030, June 2021, doi: 10.1007/s11095-504 021-03062-4), the actuation speed for hand driven skin injections is optimal at 0.9 mm/s and 56 kPa. A lower pressure and higher speed, however, are expected due to the nature of the actuation technique of the system, which motivates an optimization for maximum pressure and minimum actuation speed. In the design, the pressure and the actuation speed are related in 1D by $$p = \frac{kx - c\dot{x}}{\pi r^2} \tag{4}$$

Where p is the pump's actuation pressure, x is the total deflection of the spring after actuation, and r is the radius of the pumping chamber. It can be noted that the total deflection and the geometry of the magnet (and its mass) are constrained to the dimensions outlined infra to maintain a small footprint for the micropump. This constrains the iron trigger's maximum diameter, which suggests that the stiffness of the pumping spring has an upper limit. This is because the pumping force (and in turn the pressure generated) cannot exceed the magnetic attraction force between the magnet and the iron trigger at equilibrium. To bypass the computational expense and difficulty of simulating that magnetic attraction force, the magnetic separation force was experimentally measured to be 0.8 N with a strain gauge (PASCO PS-3202, USA) for an iron trigger with diameter d=3 mm. The resulting value for the stiffness can then be used to select an appropriate spring, and the resulting peak time can be experimentally realized by trying different damping foam thicknesses and checking the peak time with a high-speed camera.

Methods and Materials

Pump & Membrane Fabrication

The pumping chamber 146 along with the integrated MNs 158 was printed using an SLA 3D printer. Table 1 summarizes the parameters used for printing this section. The print time for this section was 46 minutes.

TABLE 1

SLA printing properties for the pumping chamber 146.

| Parameter | Value |
|---|---|
| Material | Transparent Resin (Creality) |
| Layer height [μm] | 50 μm |
| Exposure time [s] | 1 s |
| Bottom layer count | 8 |
| Bottom layer exposure time [s] | 11 s |
| Motor speed [mm/s] | 5 |

The pump's top casing 142 was printed in fused deposition modeling (FDM) on a Creality CR-10 Smart. Table 2 summarizes the printing parameters for that section.

TABLE 2

FDM printing parameters for the pump's top casing 142.

| Parameter | Value |
|---|---|
| Material | Gold PLA plus (eSUN) |
| Layer height [μm] | 200 |
| Nozzle Temperature [° C.] | 205 |
| Bed temperature [° C.] | 60 |
| Printing speed [mm/s] | 50 |

The pump's cover 140 was also printed using FDM on the same printer, but a flexible polyurethane with a shore hardness of 85 A (NinjaTek, USA) was used to allow the cover to be easily installed or removed. The self-healing inlet plug 148 was molded from Ecoflex 00-10 platinum silicone for its highest elasticity compared to other Ecoflex products. The material is also biocompatible, displays high elongation at break, and can cure relatively quickly at 60° C. in an oven. 0.2 g of each of the two components of EcoFlex 00-10 were thoroughly mixed for 1 min before being placed in a vacuum chamber for 2 min to rid the mixture of trapped air bubbles. The resulting mixture is poured into an FDM 3D printed mold and placed in an oven at 60° C. for 60 min.

High-Speed Imaging and Video Processing

The membrane's deflection speed was characterized via a high-speed imaging camera (Phantom VEO 640, Vision Labs). An open version of the pumping chamber was printed with an FDM 3D printer and attached to the top section to provide an unobstructed view of the membrane. This test section was placed on a black tabletop, and two high intensity light sources (Vision Labs, USA) were utilized to provide the camera with sufficient light for high frame rate videos. This setup can be seen in FIG. 4 in Appendix A of the priority document.

The captured video was processed on Tracker Motion Capture software. The videos were captured at 9200 frames per second at a resolution of 640×480 pixels. The membrane's velocity and position were extrapolated from the video by setting a calibration stick and an image search for the membrane's location with a frame evolution of 10%.

Preparation and Characterization of Ibuprofen Solution and Polymeric Nanoparticles In an exemplary embodiment, an ibuprofen solution was prepared by accurately weighing the drug (Ibuprofen, Sigma Aldrich, Germany) and dissolving it into phosphate buffered saline pH 7.4 to obtain a concentration of 1 mg/ml. For the polymeric nanoparticles, PLGA was dissolved in ethyl acetate and the drug was added until complete dissolution. The organic solution was then added to an aqueous 1% PVA (Polyvinyl alcohol, Sigma Aldrich, Germany), and the mixture was exposed to ultrasoncation using a probe sonicator for 4 minutes in an ice bath. The resulting emulsion was then directly transferred to a round bottom flask and fixed to a rotary evaporator for the evaporation of the organic solvent resulting in the polymeric nanoparticles suspended in the aqueous PVA solution. The particles were characterized for their particle size and zeta potential after 10 folds dilution using dynamic light scattering using Zetasizer Nano ZN (Malvern Panalytical Ltd, United Kingdom) at a fixed angle of 173° at 25° C. The samples were analyzed in triplicates. The shape and surface morphology of the PLGA nanoparticles was then examined using scanning electron microscopy (Hitachi S 2460N, Tokyo, Japan). One drop of the nanoparticles' dispersion was placed on the surface of an aluminum stub, left to dry overnight, and then sprayed with a gold coat before being examined by the scanning electron microscope.

Ex-Vivo Skin Deposition Study

Franz diffusion cells were used for the study of skin deposition with the receptor compartment filled with phosphate buffered saline (pH7.4) and maintained at 37° C. throughout the experiment duration. Skin was excised from the back of sacrificed Sprague Dawley rats, shaved with electric clippers and then mounted between the donor and receptor compartments of the Franz cell. The pump was filled with either the ibuprofen solution or the nanoparticles and fixed with a 3D printed fixture on top of the rat skin (see FIG. 5 in Appendix A of the priority document). The pump was actuated, resulting in the injection of the formulation into the skin. To test the efficacy of the pumping mechanism, control trials were carried out using the bottom section of the pump containing the MNs only. The skin was then collected and divided into three different layers for extraction. The first layer (the stratum corneum) was separated by tape stripping of the skin for 15 consecutive times and all the strips were collected in one container. The second and the third layers (epidermis and dermis) were simply separated by forceps and each layer was extracted using ethanol. The extracts of the three layers were then injected into the High-Performance Liquid Chromatography (HPLC) testing rig for the detection of the concentration of the drug in the respective skin layers according to a previously described technique.

MNs Array Optimization

A numerical analysis approach was utilized to simulate different numbers of MN arrays' penetration. The combination of the largest number of MNs and maximum penetration was selected for the design. The following sections outline the methodology employed for these simulations.

Problem Setup

The MN array used was optimized for maximum penetration into the skin without wrinkling. Numerical FEM based simulations were conducted to reduce the number of design trials. Two parameters were of specific interest: the number of needles in the array and the spacing between those needles. Five configurations of needle arrays constrained by the geometry of the pump's base were applied to simulate the effect of these parameters on human skin. Table 3 shows the number of needles and spacing for each configuration simulated. The simulations were conducted using the Explicit Dynamics package in Ansys.

TABLE 3

MN array configurations utilized for simulations.

| Configuration number | Number of Needles | Spacing between Needles (mm) |
|---|---|---|
| 1 | 12 | 2 |
| 2 | 20 | 1.8 |
| 3 | 20 | 1.6 |
| 4 | 30 | 1.3 |
| 5 | 48 | 1 |

Geometry Preparation

The geometry of each configuration has two parts as indicated in FIG. 6 as shown in Appendix A of the priority document. The upper part is the MNs, and the lower part is a rectangular box that represents human skin. The study focused on the penetrability of the needles and their effect on skin; accordingly, the rest of the system was not modeled to decrease computational effort.

Material Model

Human skin is a composite multi-layered structure that normally behaves mechanically as a viscoelastic material. In biomechanical testing, skin acts homogenously and can be approximated as a coherent structure. As discussed earlier, the skin has two main layers: epidermis and dermis—with variations in thickness of each layer depending on factors like age, genetics, and physical condition. The designed MNs are required to penetrate the epidermis and part of the dermis layer. Accordingly, the modeled skin was chosen to be isotropic with a thickness of 1 mm.

The skin material model was approximated to be linear and highly elastic (high Poisson ratio) with failure criteria determined to be 10 percent extra strain above yield strain. An elastic modulus of 65 MPa and a Poisson ratio of 0.48 were used. PLA was selected for the MNs' material with an elastic modulus of 3.5, an ultimate tensile strength of 60 MPa, and 2.5% elongation at break.

Results: MN Array

All MN configurations successfully penetrated the required thickness with direct material cut or removal. Higher values of stress were only local to the location of the MNs' penetration with no effect on global skin structure. Configuration 5, however, showed continuous wrinkling of the skin between the subsequent MNs because of their smaller spacing. This wrinkling results in an undesirable decrease of the penetration depth of the MNs into the skin. It may also cause skin irritation which will cause discomfort to the patient. Configuration 4 was therefore selected as the optimum MNs array configuration since it provides the highest number of MNs that penetrate the skin with minimal skin wrinkling.

Results: Membrane Speed

The results obtained for the membrane position and deflection from the high-speed camera photography (FIG. 4A-B). It is observed that the membrane reaches its maximum deflection of 3.6 mm in around 13 ms with a maximum speed of 0.45 m/s and average speed of ~0.28 m/s. The variations shown in the speed trend can be attributed to small errors in tracking the exact pixel at the tip of the membrane in the motion tracking software.

Modal Analysis

A modal analysis was conducted to ensure that the iron-magnet attraction does not accidentally separate-thereby triggering the micropump-during operation, which can render the device dangerous to use in daily operations like driving a car, running, etc. Linear modal and harmonic vibrational analysis simulations were conducted using the Ansys Mechanical package. The analysis showed a first, second, and third modes at 548.8 Hz, 646.33 Hz, and 795.3 Hz, respectively. This is sufficiently far from the typical car vibration, running, or typical daily activities.

Characterization of Ibuprofen Nanoparticles

The nanoparticles were successfully prepared and were found to be spherical, uniform negatively charged particles. The particle size is 215+5.8 nm, polydispersity index is 0.03±0.005, and the zeta potential is −18+2.5. An SEM image of the nanoparticles can be seen in FIG. 9 of Appendix A in the priority document.

Ex Vivo Test

The results obtained for the ex vivo test 5 minutes after the pump actuation are shown in FIG. 10 of Appendix A in the priority document. The results show, on average, almost twice the total percentage of nanoparticles formula (21.4%) deposited in the skin compared to that of the drug solution (11.3%). The control (without the pumping mechanism) exhibited a total deposition percentage of 2.5%, indicating that the pumping mechanism is functional. The conclusions drawn from these results are discussed in the following sections.

Penetration Depth

The dermis layer showed the highest percentage of deposition compared to the stratum corneum and the epidermis. This is expected because the MNs were designed to pierce the stratum corneum and the epidermis. The pointed shape of the MNs and the shape of their base explain the lower percentages deposited in the stratum corneum and the epidermis. The control MNs array without the pumping mechanism also exhibited a similar trend, with a higher, albeit small (2.3%), deposition percentage at the dermis layer in the short time frame. This demonstrates that the hollow MNs utilized are effective in delivering the drug to the dermis layer. Alone, however, these hollow MNs were not sufficient for substantial drug deposition at a short time frame.

Effect of Nanoencapsulation

The polymeric nanoparticles displayed a higher total deposition percentage than that exhibited by the drug solution. This is remarkable because polymeric nanoparticles, to the best of the inventors' knowledge, were not introduced to the skin through a micropumping system before, and thus this comparison between an untreated model drug and a polymeric nanoparticle version of it is unique. It is documented in the literature that the utilized polymeric nanoparticles excel in the sustained (long term) release and deposition of a drug into the skin relative to an untreated drug solution. This is anticipated because the particles' nanometer size allows them to travel more easily into the skin's inherently porous structure. It can be concluded, however, that this process can be catalyzed, at least initially, through a micropumping mechanism that provides the particles with a sufficient initial velocity and pressure to traverse through the skin layers.

IN CONCLUSION

A novel 3D printed, MN integrated micropump combined with polymeric nanoparticles for rapid TDD is successfully realized in this work. The micropumping mechanism utilized a low current SMA spring to trigger its actuation, and the MNs' geometry was optimized using FEA techniques. Polymeric nanoparticles were developed for a model drug and loaded into the micropump for an ex vivo rat skin deposition experiment. The system exhibited a considerable improvement in the total percentage of polymeric nanoparticles deposited in rat skin compared to a traditional drug solution in a short time frame. In just 5 minutes, the system delineated a 21.4% total deposition of the drug nanoparticles into the skin. This can be compared to only 2.3% total deposition in the same time frame for the nanoparticles without the micropumping mechanism. This ascertains the efficacy of this new concept of combining polymeric nanoparticles with a microneedle integrated micropump.

The short-term response, small footprint, demonstrated robustness, and low power consumption of the system can make it potentially very useful for insulin administration. The system can be integrated into a wearable device with a glucose sensor for automated transdermal insulin administration.

What is claimed is:

1. A transdermal drug delivery method, comprising:

(a) having a transdermal drug delivery system comprising:

(i) a triggering subsystem having a Shape Memory Alloy (SMA) spring attached to and above an iron trigger, (ii) a drug delivery subsystem situated below the triggering subsystem, wherein the drug delivery subsystem has a preloaded pumping spring and a damping foam situated above a magnet, and as such the preloaded pumping spring and the damping foam are positioned in between a bottom side of the iron trigger and a top side of the magnet, and a bottom side of the magnet is attached to an elastic membrane lining, and (iii) a microneedle subsystem having a pump chamber containing a drug, the elastic membrane lining an inside of the pump chamber, and an array of hollow microneedles at a bottom of the pump chamber; and (b) controlling a current to the SMA spring resulting in the SMA spring to heat and shrink to an original length of the SMA spring, thereby separating the SMA spring and the attached iron trigger from the magnet resulting in extension of the preloaded pumping spring and the damping foam, wherein the extension of the preloaded pumping spring and the damping foam results in pushing the elastic membrane lining that pushes the drug in the pump chamber through the array of hollow microneedles, which are in contact with a skin portion, pushing the drug via the array of hollow microneedles into the skin portion.

2. The transdermal drug delivery method as set forth in claim 1, wherein the drug is a nanoencapsulated drug.

* * * * *